United States Patent
Yetik

(10) Patent No.: US 9,687,197 B2
(45) Date of Patent: Jun. 27, 2017

(54) SYSTEM FOR VISUALIZING BODY AREAS

(71) Applicant: Huseyin Yetik, Istanbul (TR)

(72) Inventor: Huseyin Yetik, Istanbul (TR)

( * ) Notice: Subject to any disclaimer, the term of this patent is extended or adjusted under 35 U.S.C. 154(b) by 17 days.

(21) Appl. No.: 14/888,456

(22) PCT Filed: Apr. 16, 2014

(86) PCT No.: PCT/TR2014/000114
§ 371 (c)(1),
(2) Date: Nov. 2, 2015

(87) PCT Pub. No.: WO2014/078806
PCT Pub. Date: Nov. 6, 2014

(65) Prior Publication Data
US 2016/0106369 A1  Apr. 21, 2016

(30) Foreign Application Priority Data
May 2, 2013  (TR) ................. 2013/05176

(51) Int. Cl.
*A61B 3/14* (2006.01)
*A61B 5/00* (2006.01)
(Continued)

(52) U.S. Cl.
CPC ........ *A61B 5/6898* (2013.01); *A61B 1/00188* (2013.01); *A61B 1/227* (2013.01);
(Continued)

(58) Field of Classification Search
CPC ....... A61B 3/0083; A61B 3/12; A61B 3/1208; A61B 3/125; A61B 3/14; A61B 3/145; A61B 3/185
(Continued)

(56) References Cited

U.S. PATENT DOCUMENTS

| 9,325,884 B2 * | 4/2016 | Fletcher | H04M 1/21 |
| 2011/0009163 A1 * | 1/2011 | Fletcher | G02B 21/0008 455/556.1 |

(Continued)

FOREIGN PATENT DOCUMENTS

| EP | 0868878 | 10/1998 |
| WO | WO 2006/083081 | 8/2006 |
| WO | WO 2012/058641 | 5/2012 |

OTHER PUBLICATIONS

International Search Report of PCT/TR2014/000114, Mailed Oct. 8, 2014.

*Primary Examiner* — Huy K Mai
(74) *Attorney, Agent, or Firm* — Mark M. Friedman

(57) ABSTRACT

The invention is a system comprising an adaptor (10) which comprises an inner chamber (111) into which electronic recording devices that can record images such as smart phones, pocket computer, tablet computer can be placed and a space (112) provided on the location that comes across with the camera of the electronic recording device, characterized in that, said single adaptor (10) comprises a mounting part (113) located on the front side of the adaptor (10) and focusing optic units connected to said mounting part (113) during application and have a lens assembly chosen in accordance with the body part to be visualized, for being used in more than one application such as biomicroscopy, indirect ophthalmoscopy, otoscopy, dermatoscopy and colposcopy.

10 Claims, 4 Drawing Sheets

(51) Int. Cl.
*A61B 1/227* (2006.01)
*A61B 1/303* (2006.01)
*A61B 3/12* (2006.01)
*A61B 1/00* (2006.01)
*G02B 21/02* (2006.01)
*G02B 21/36* (2006.01)
*G03B 17/56* (2006.01)

(52) U.S. Cl.
CPC ............ *A61B 1/303* (2013.01); *A61B 3/12* (2013.01); *A61B 3/14* (2013.01); *A61B 5/0077* (2013.01); *A61B 5/441* (2013.01); *G02B 21/025* (2013.01); *G02B 21/362* (2013.01); *A61B 5/44* (2013.01); *A61B 2560/0431* (2013.01); *A61B 2560/0443* (2013.01); *G03B 17/565* (2013.01)

(58) Field of Classification Search
USPC .................. 351/206, 210, 216, 219, 245
See application file for complete search history.

(56) References Cited

U.S. PATENT DOCUMENTS

2012/0320340 A1    12/2012   Coleman, III
2013/0083185 A1     4/2013   Coleman, III \* cited by examiner

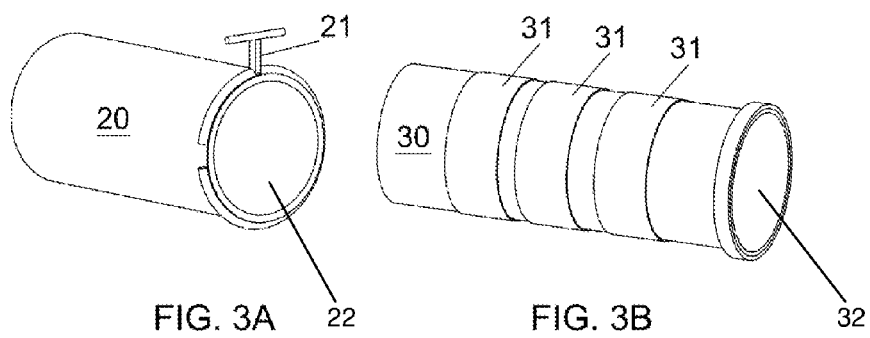

SYSTEM FOR VISUALIZING BODY AREAS

TECHNICAL FIELD

The invention relates to recording, archiving, easy sharing of photographs and/or videos of body areas such as eye, skin, nose, ear, throat, cervix etc. in medical fields like ophthalmology, dermatology, otorhinolaryngology being in the first place.

PRIOR ART

For recording, archiving, easy sharing of photographs and/or videos of body areas such as eye, skin, nose, ear, throat, cervix etc. in medical fields like ophthalmology, dermatology, otorhinolaryngology, various types of electronic devices are used.

Devices used in current applications are very large. Additionally, they are not easily transportable. For instance, wheeled stands are needed to carry them from one room to another within the same clinic. It is impossible for the doctor and/or operator to carry these devices in a small bag or in his/her pocket. Moreover, these devices are very expensive.

For each usage area, different devices are used. For example in eye diseases, slit lamp biophoto is used for the front segment of the eye which can make visualization under slit-lamp, fundus camera is used to visualize the back segment of the eye and the for indirect ophthalmoscopic retina visualization, retina cameras with different brands are used Additionally, especially the images obtained in retina visualization are not clear enough. In these devices obtaining, capturing, focusing and autofocusing the image is very hard in technical terms. Most of them operate with an additional computer (desktop or laptop). To sum up, there is no portable application in prior art.

Patent application US2012287402A1 describes a slit lamp adaptor for portable cameras. Another patent application WO2012177544A1 describes a smart phone adaptor for ophthalmoscope device. Said patent application is a device which connects a portable camera such as a smart phone with a handheld ophthalmoscope and thus provides a joint use. In medical terms it combines direct ophthalmoscopy method with a portable camera. Said adaptors are not for mounting various medical devices (biomicroscope, indirect ophthalmoscope, otoscope, dermatoscope, colposcope etc.). They are used just for a single type of device and single type of medical examination. Additionally, the structure of said invention requires a separate handheld ophthalmoscope device for ophthalmoscopy procedure.

Consequently, due to negative sides mentioned above, there is need for an embodiment which will overcome the drawbacks mentioned above.

BRIEF DESCRIPTION OF THE INVENTION

The present invention is an adaptor used for medical purposes which overcomes all the disadvantages mentioned above and provides additional advantages in the related technical field.

The main object of the invention is to provide a portable visualization and recording system for the front and back segment of the eye, by connecting electronic recording devices such as smart phones, tablet computers etc. to the biomicroscope. Another object of the invention is to provide indirect ophthalmoscope, dermatoscope, otoscope, colposcope devices which use the light source of electronic recording device as an illumination source and which provides a portable digital recording feature by special focusing lens systems with proper diopter attached to the front part of the camera, without requiring medical devices such as ophthalmoscope, otoscope, dermatoscope and colposcope.

Another object of the invention is to provide a single unit which can make visualization with a single adaptor connected to an electronic recording device in more than one technique such as biomicroscopy, indirect ophthalmoscopy, otoscopy, dermatoscopy and colposcopy.

In order to realize all the objectives which are mentioned above and will be clear from the detailed description below, a system comprising an adaptor is provided which comprises an inner chamber into which electronic recording devices that can record images such as smart phones, pocket computer, tablet computer can be placed and a space provided on the location that comes across with the camera of the electronic recording device. Said system comprises focusing optic units which comprise a mounting assembly located on the front side of the adaptor and a lens assembly connected to said mounting part during application and chosen in accordance with the body part to be visualized, for being used in more than one application such as biomicroscopy, indirect ophthalmoscopy, otoscopy, dermatoscopy and colposcopy.

According to another preferred embodiment of the invention, said focusing optic units are a biomicroscope attachment which will be used for biomicroscopy, an indirect ophthalmoscope attachment which will be used for ophthalmoscopy, an otoscope attachment which will be used for otoscopy, a dermatoscope which will be used for dermatoscopy and a colposcope which will be used for colposcopy.

In another preferred embodiment of the invention, the dimensions of said focusing optic unit are adjusted according to the characteristics of the focusing distance of the camera of the electronic recording device.

In another preferred embodiment of the invention, said focusing optic units comprise zoom lenses which are fixed and replaceable.

In another preferred embodiment of the invention, the biomicroscope attachment comprises an adjustable pressing element for mounting various types of biomicroscopes to the body.

In another preferred embodiment of the invention, the indirect ophtalmoscope attachment comprises an optic part which can make focusing in order to take indirect ophtalmoscopic retina images.

DESCRIPTION OF THE FIGURES

FIG. 3a—View of biomicroscope attachment.
FIG. 3b—View of indirect ophthalmoscope attachment.

REFERENCE NUMBERS

Figure 1:
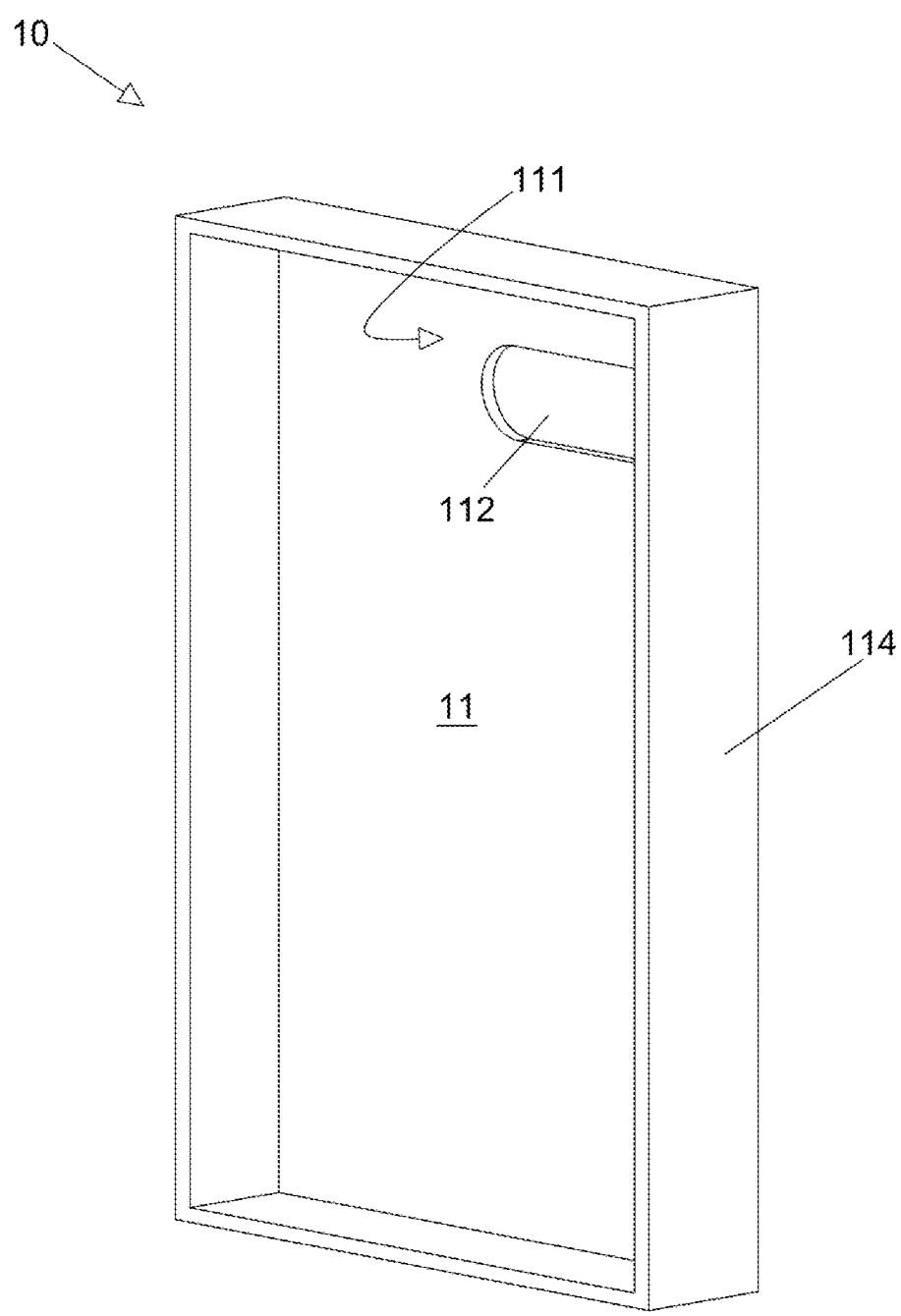
FIG. 1—General view of the main adaptor unit
FIG. 2—General view of the main adaptor from a different angle.

10 Adaptor
11 Body
111 Inner chamber
112 Space
113 Mounting part
114 Side surface 20 Biomicroscope attachment
21—Pressing element
30 Indirect ophtalmoscope attachment
31 Optic part
40 Otoscope attachment
41 Optic part
50 Dermatoscope attachment
51 Optic part
60 Colposcope attachment
61 Optic part

DETAILED DESCRIPTION OF THE INVENTION

In this detailed description, novelty subject to the invention is explained solely for a better understanding of the subject, without generating any restrictive effect. Accordingly, in the description and figures below, an adaptor (10) which provides the usage of electronic recording devices such as smart phones, pocket computers, tablet computers etc. (hereinafter, they will be called electronic recording device) in biomicroscopy, indirect ophthalmoscopy, otoscopy, dermatoscopy, colposcopy procedures and focusing optic units configured according to this adaptor, are described.

In FIG. 1, a perspective back view of the adaptor (10) is given. Accordingly, the adaptor (10) has a body (11) configured in such a way that the electronic device can be placed into it. Said body (11) preferably has a rectangular shape and comprises an inner chamber (111) into which the electronic device is placed. Said inner chamber (111) is formed by four side surfaces (114) surrounding the chamber.

Figure 2:
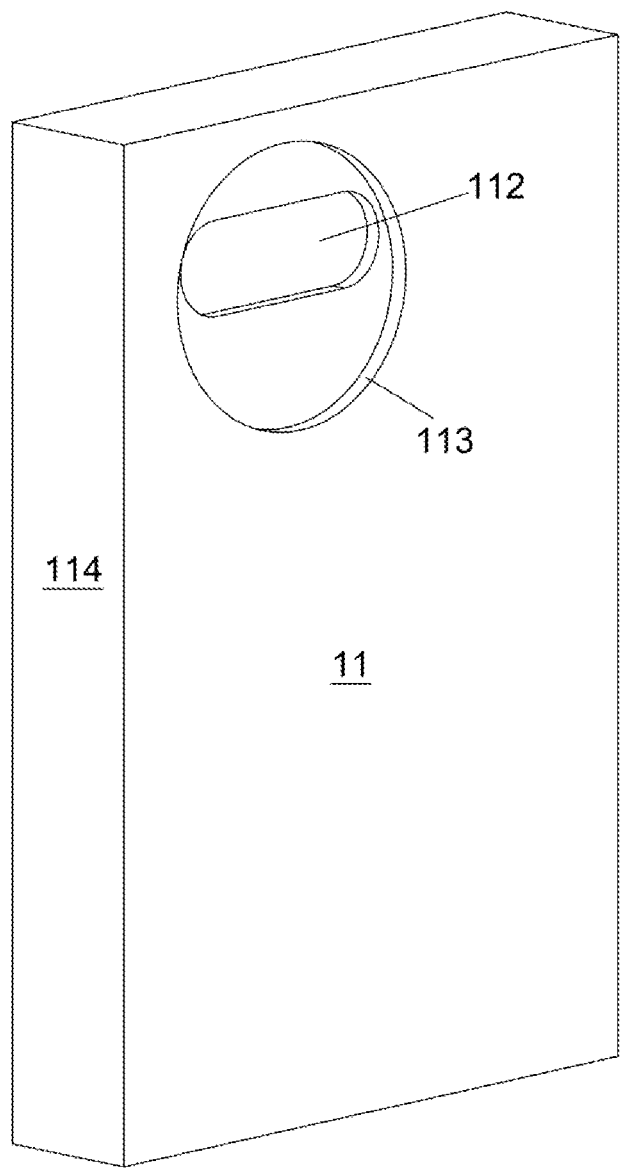

In FIG. 2 the view of the adaptor (10) from a different angle is given. In this figure, the front surface of the body (11) is seen. Accordingly, there is a space (112) at the part of the body (11) where the cameras of the electronic recording devices come across with Through this space (112), the electronic recording devices can take videos and/or pictures with the camera. A mounting part (113) is provided on the body (11) to provide the connection of the medical devices such as biomicroscope, indirect ophthalmoscope, otoscope, dermatoscope and colposcope to the body (11).

In FIGS. 3a, 3b, 3c, 3d, and 3e, views of different optic focusing units are given. Said focusing optic units comprise an optic part. The optic part comprises lenses with appropriate features which can make focusing in order to take images according to the usage area of the focusing optic unit.

In FIGS. 3a, 3b, 3c, 3d, and 3e, the general views of a biomicroscope attachment (20), an indirect ophthalmoscope attachment (30), an otoscope attachment (40), a dermatoscope attachment (50), a colposcope attachment (60) are given respectively. The parts of said attachments (20, 30, 40, 50) connected to the mounting part (113) are identical and they are shaped compatible with the mounting part (113).

In accordance with the FIG. 3a, the biomicroscope attachment (20) attached to the mounting part (113) of the adaptor (10) is connected to the body (11) from the mounting part (113). During mounting, it is placed in such a way that it will be compatible with the electronic recording device present in the inner chamber (111) of the body (11). Then, one of the oculars of the microscope is attached to the attachment (20) of the biomicroscope. Biomicroscope attachment (20) comprises a pressing element (21). If the device will be used to visualize the front and back segments of the eye under the biomicroscope (slit lamp), the biomicroscope is attached to the biomicroscope attachment (20) by being adjusted with the pressing element (21) compatible with the biomicroscope brand to be used.

In accordance with FIG. 3b, aspheric lens whose dioptre value (20, 28, 56D etc.) can be changed according to the indirect ophthalmoscopic visualization area and the optic part (31) which can make zooming, focusing and autofocusing are added and thus, indirect ophthalmoscopic retina images can be taken. The autofocusing process of the image is carried out by the camera of the electronic recording device. The devices may also be used in medical visualization if their cameras have the optical zoom feature. In the present invention, the fixed zoom or optic zoom (31) feature (depending on the needs) and the width of the area visualized on the retina are dependant on the features of the lens used in the attachment (30) and the features of the optic part (31) to which the lens is connected. The length of the indirect ophthalmoscope attachment (30) is manufactured so that it is adjusted according to the focusing distance of the camera present on the used electronic device.

Figure 3C:
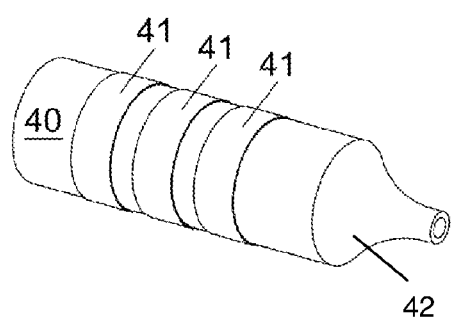
FIG. 3c—View of otoscope attachment.

In accordance with FIG. 3c, otoscope attachment (40) is a focusing optic unit focusing the inner ear. The optical part (41) of the otoscope attachment (40) comprises an aspheric lens which has a fixed or adjustable zoom and which is solid mounted according to the needs, and whose dioptre value (20, 28, 56D etc.) can be changed. The length of this attachment (40) is manufactured so that it is adjusted according to the focusing distance of the camera present on the used electronic device.

Figure 3D:
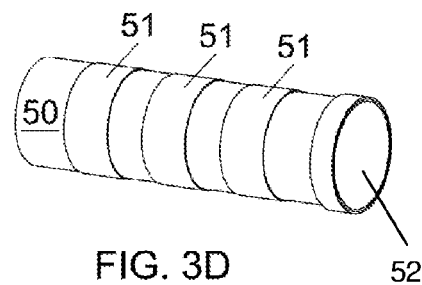
FIG. 3d—View of dermatoscope attachment.

In accordance with FIG. 3d, dermatoscope attachment (50) is a focusing optic unit focusing the skin area. The optical part (51) of the dermatoscope attachment (50) comprises an aspheric lens which has a fixed or adjustable zoom and which is solid mounted according to the needs, and whose dioptre value (20, 28, 56D etc.) can be changed. The length of this attachment (50) is manufactured so that it is adjusted according to the focusing distance of the camera present on the used electronic recording device.

Figure 3E:
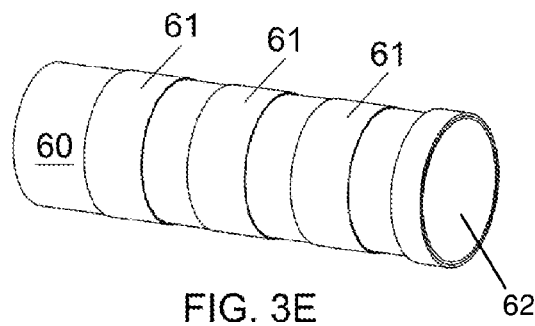
FIG. 3e—View of colposcope attachment.

In accordance with FIG. 3e, colposcope attachment (60) is the focusing optic unit focusing the cervical area The optical part (61) of the colposcope attachment (60) comprises an aspheric lens which has a fixed or adjustable zoom and which is solid mounted according to the needs, and whose dioptre value (20, 28, 56D etc.) can be changed. The length of this attachment (60) is manufactured so that it is adjusted according to the focusing distance of the camera present on the used electronic recording device.

Consequently, by the virtue of the invention, after placing the electronic recording device into the inner chamber (111), one of the attachments appropriate for the visualization area is attached to the front of the device camera, namely to the mounting part (113), and thus, the images can be taken. The body part to be visualized is illuminated by the light source of the device camera. The light of the illumination source passes through the related focusing optic unit and reaches to the area to be visualized. Then, the body part is visualized by using the camera feature of the electronic recording device and the images are recorded to the memory unit of the electronic recording device. Therefore, the invention is portable and can be carried in the pocket and may be used in many fields of medicine.

The invention claimed is:

1. A system for visualizing human body areas, comprising:
   a plurality of determined focusing optic units; and
   an adaptor (10) comprises a body (11), wherein the body (11) further comprises:

an inner chamber (111) that is adapted to receive at least one of a plurality of electronic recording devices that record images, wherein the plurality of electronic recording devices are smart phones, pocket computer, or tablet computer;

a space (12) that is formed on a location that comes across with a camera of the received electronic recording device; and a mounting part (113) that is located on a front side of body (11) of the adaptor (10), wherein the front side of the body (11) is in opposite side of the inner chamber (111), wherein at least one of the plurality of determined focusing optic units is adapted to connect with said mounting part (113), wherein each of the plurality of determined focusing optic units comprises:

a coupling part that is adapted to connect to said mounting part (113) during visualization of body parts, and a lens assembly that is selected in accordance with a respective body part to be visualized, wherein the plurality of determined focusing optic units are adapted to be used in biomicroscopy, indirect ophthalmoscopy, otoscopy, dermatoscopy and olposcopy, wherein said coupling part of the plurality of determined focusing optic units is identical and shaped compatible with said mounting part (113).

2. The system according to claim 1, wherein the plurality of determined focusing optic units are a biomicroscope attachment (20) that is adapted to be used for biomicroscopy, an indirect ophthalmoscope attachment (30) that is adapted to be used for ophtalmoscopy, an otoscope attachment (40) that is adapted to be used for otoscopy, a dermatoscope attachment (50) that is adapted to be used for dermatoscopy, and a colposcope attachment (60) that is adapted to be used for colposcopy.

3. The system according to claim 2, wherein the biomicroscope attachment (20) comprises an adjustable pressing element (21) to adjust diameter of the biomicroscope attachment for mounting of biomicroscopes to the body (11).

4. The system according to claim 2, wherein the indirect ophthalmoscope attachment (30) comprises an aspheric lens (32) that is placed inside of an optic part (31), wherein the optic part (31) makes focusing in order to take indirect ophthalmoscopic retina images, wherein autofocusing of the retina images is carried out by the camera of the received electronic recording device.

5. The system according to claim 2, wherein the otoscope attachment (40) comprises an aspheric lens (42) that is place inside of an optic part (41), wherein the optic part (41) makes focusing in order to take otoscopic images, wherein autofocusing of the otoscopic images is carried out by the camera of the received electronic recording device.

6. The system according to claim 2, wherein the dermatoscopic attachment (50) comprises an aspheric lens (52) that is place inside of an optic part (51), wherein the optic part (51) makes focusing in order to take dermatoscopic images, wherein autofocusing of the dermatoscopic images is carried out by the camera of the received electronic recording device.

7. The system according to claim 2, wherein the colposcope attachment (60) comprises an aspheric lens (62) that is place inside of an optic part (61), wherein the optic part (61) makes focusing in order to take colposcopic images, wherein autofocusing of the colposcopic images is carried out by the camera of the received electronic recording device.

8. The system according to claim 1, wherein a length of each of the plurality of determined focusing optic unit are adjusted according to the characteristics of the focusing distance of the camera of the plurality of electronic recording devices by twisting the plurality of determined focusing optic unit.

9. The system according to claim 1, wherein the plurality of determined focusing optic units comprise zoom lenses (22, 32, 42, 52, 62) which are fixed inside of the lens assembly of the plurality of determined focusing optic units, wherein the zoom lenses (22, 32, 42, 52, 62) are aspheric lenses and replaceable.

10. The system according to claim 1, each of the plurality of determined focusing optic units comprises an optic part (31, 41, 51, 61) to receive said lens assembly.

* * * * *